United States Patent
De Jonge et al.

(10) Patent No.: US 6,768,020 B2
(45) Date of Patent: Jul. 27, 2004

(54) METHOD FOR THE CATALYTIC CONVERSION OF ORGANIC CARBONATE AND THE USE OF A LANTHANUM CATALYST THEREFOR

(75) Inventors: Johannes Petrus De Jonge, Amsterdam (NL); Jean-Paul Lange, Amsterdam (NL); Ingrid Maria Van Vegchel, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/292,173

(22) Filed: Nov. 12, 2002

(65) Prior Publication Data

US 2003/0097016 A1 May 22, 2003

(30) Foreign Application Priority Data

Nov. 13, 2001 (EP) .............................................. 01309571

(51) Int. Cl.⁷ .......................... C07C 27/26; C07C 29/09; C07C 69/96
(52) U.S. Cl. ....................................... 558/277; 568/913

(58) Field of Search ................................ 558/277, 260; 568/13

(56) References Cited

U.S. PATENT DOCUMENTS 5,847,189 A 12/1998 Tojo et al. ................... 558/277

FOREIGN PATENT DOCUMENTS

| EP | 599287 | 6/1994 | ............ C07C/68/06 |
| EP | 893428 | 1/1999 | ............ C07C/68/06 |

OTHER PUBLICATIONS

Database WPI, Section Ch. Week 199840, Derwent Publications Ltd., London, GB; Class E17, An 1998–462798 XP002192191 & JP 10 195003 A (Mitsubishi Chem Corp), Jul. 28, 1998 abstract.

*Primary Examiner*—Taofiq Solola

(57) ABSTRACT

A method for the catalytic conversion of organic carbonate, wherein organic carbonate is contacted with alcohol and/or water in the presence of a lanthanum catalyst comprising at least about 7 wt. % of lanthanum supported on a support.

14 Claims, No Drawings

US 6,768,020 B2

METHOD FOR THE CATALYTIC CONVERSION OF ORGANIC CARBONATE AND THE USE OF A LANTHANUM CATALYST THEREFOR

FIELD OF THE INVENTION

The present invention relates to a method for the catalytic conversion of organic carbonate and to the use of a lanthanum catalyst in such a method for the catalytic conversion of organic carbonate.

BACKGROUND OF THE INVENTION

JP-08-176071 relates to the catalytic conversion of a cyclic alkylene carbonate into an acyclic carbonate and a diol. In this conversion reaction use is made of a catalyst comprising mixed metal oxides consisting of Co and a metal oxide selected from the group consisting of Y, La, Ce, Pr, Nd or Sm. Preferred are Y and Sm.

JP-07-330685 relates to a method for the production of dialkyl carbonate in which an alkylene carbonate is reacted with an alcohol in the presence of a specific catalyst. This catalyst comprises a metal oxide of a metal from group IIIB of the Periodic Table. It may be a rare earth metal oxide, such as an oxide of Sc, Y, Sm, Pr, Nd and Eu. For reasons of reaction activity are preferred the oxides of Y and Sm.

JP-2001-2624 relates to a method for the preparation by transesterification of a symmetrical dialkyl carbonate using a solid catalyst comprising as the active ingredient oxides of elements selected from group III of the Periodic Table, consisting of lanthanides, actinides, Sc and Y.

EP-A-0,599,287 describes a process for preparing dialkyl carbonate which comprises subjecting an alkylene carbonate and an alcohol to a transesterification to form a dialkyl carbonate, the characteristic feature residing in that a catalyst containing at least one rare-earth oxide as the catalytically active component is used. Several examples for catalysts consisting of lanthanum-oxide solely or of mixed rare-earth oxides comprising lanthanum are described, as well as two catalysts comprising an amount of lanthanum oxide of 4.3 wt. % based on lanthanum carried- on γ-alumina, and an amount of lanthanum oxide of 6.4 wt. % based on lanthanum carried on silica gel. A problem with catalysts consisting of rare earth oxides is that the surface area of these catalysts is limited. As a result, only a small proportion of the lanthanum oxide particles will actually participate in the reaction. A problem with lanthanum oxides in the support is that their strong hygroscopic behavior may mean that their stability towards feeds comprising, water is limited causing swelling of the particles.

The present invention has for its object to provide a method for the catalytic conversion of organic carbonate having a high reaction activity and has a low rate of metal leaching from the catalyst.

SUMMARY OF THE INVENTION

This is obtained with the method according to the invention for the catalytic conversion of organic carbonate, wherein organic carbonate is contacted with alcohol and/or water in the presence of a catalyst comprising lanthanum compound in an amount of at least about 7 wt. % of lanthanum supported on a support.

DETAILED DESCRIPTION OF THE EMBODIMENTS

This lanthanum catalyst comprises lanthanum compound supported on a support. This lanthanum compound is $La_2O_3$ or a precursor thereof. Under reaction conditions this lanthanum compound may be temporarily and/or reversibly be converted due to the reaction conditions into lanthanum hydroxide $(La(OH)_3)$, lanthanum oxyhydroxide $(LaO(OH))$ and/or corresponding alcoholate specious such as $(La(OR)_3$ or $LaO(OR))$.

As a support for the lanthanum catalyst any suitable support may be used which is substantially inert under the reaction conditions and is provided with sufficient mechanical strength. Potential supports comprise clay minerals, inorganic supports such as $Al_2O_3$, $SiO_2$, $MgO$, $TiO_2$, $ZrO_2$, ZnO and mixtures thereof. Other examples are a kaolinite, a hallosyte, a chrysotile, a mont-morillonite, a beidelite, a saponite, a hectorite, a sauconite, a muscovite, a phlogopite, a biotite, a hydrotalcite, and talc, etc. Particularly preferred are the inorganic supports selected from $Al_2O_3$, $SiO_2$, MgO, $TiO_2$, $ZrO_2$, ZnO and mixtures thereof.

Supporting the catalysts on a suitable support has the advantage of allowing optimization of the surface area and of the pore structure of the catalyst. Furthermore, also the overall strength and the overall structure of the catalyst particles may be optimized with respect to process parameters such as the pressure drop in reactors packed with catalyst particles.

The lanthanum catalyst comprises the lanthanum compound in an amount such that the lanthanum catalyst exhibits its catalytic reactivity. Generally, the lanthanum catalyst comprises at least about 7 wt. % of lanthanum, preferably more that about 7 wt. % of lanthanum, more preferably at least about 8 wt. % of lanthanum, more preferably more than about 8 wt. % of lanthanum, even more preferably at least about 10 wt. % of lanthanum. The lanthanum catalyst further preferably comprises at most about 40 wt. % of lanthanum, more preferably at most about 30 wt. %, even more preferably less than about 30 wt. %, and most preferably at most about 20 wt. % of lanthanum. The amounts of lanthanum are to be calculated as the amount of metal on total catalyst. Catalysts comprising amounts of lanthanum oxide below a lanthanum content of about 7 wt. % generally do not exhibit the catalytic activity required for use in a process on an industrial scale, whereas catalysts comprising amounts of lanthanum above about 40 wt. % will not exhibit an improved catalytic activity, however will be more costly. Most preferably, the catalyst comprises of from about 7 to about 40 wt. % lanthanum, preferably of from about 8 to about 30 wt. % lanthanum per gram support, and most preferably of from about 10 to about 20 wt. % lanthanum.

Suitably, the support will have a surface area (BET-surface area) of from about 10 to about 500 $m^2/g$.

Preferably, the support will have a surface area of from about 20 to about 400 $m^2/g$, more preferably of from about 30 to about 350 $m^2/g$, and most preferably of from about 50 to about 320 $m^2/g$.

Furthermore, the difference in the performance of supports with similar surface areas may also be attributed to a different factor. Without wishing to be bound to any particular theory, it is believed that the predominantly basic lanthanum oxides may be more evenly distributed on a neutral or acidic support surface rather than on a surface comprising more basic sites. Therefore, supports exhibiting an amphoteric or slightly acidic behaviour are preferably used for the purpose of the present invention, in particular alumina supports.

Conveniently, the catalyst may comprise several catalytically active oxides of metals besides La and those comprised in the support itself. However, the presence of other metals may distort the lanthanum oxide surface, which may result in a decreased stability towards leaching and thus limited catalyst lifetime, and/or and increase in side reactions leading to a reduced selectivity. Therefore, the catalysts useful for the present invention preferably comprise solely lanthanum oxide besides those metal oxides which can be present in the support itself.

The catalytic conversion of organic carbonate may be a catalytic reaction with alcohol (alcoholysis and in particular a methanolysis). The catalytic conversion may be a reaction with water (hydrolysis). Finally, the catalyst allows a catalytic conversion comprising both an alcoholysis and a hydrolysis.

The organic carbonate which may be used as starting material in the method according to the invention, comprises ($C_1$–$C_5$) dialkyl carbonates, wherein the alkyl groups (straight, branched and/or cyclic) may be the same or different, such as methyl, ethyl and propyl;

($C_5$–$C_7$) diaryl carbonates, wherein the aryl groups may be the same or different, such as phenyl;
($C_1$–$C_5$) alkyl ($C_5$–$C_7$) aryl carbonates, wherein the alkyl and the aryl group are as defined above;
($C_1$–$C_{10}$) alkylene carbonates (cyclic carbonates) such as the carbonates of ethylene, propylene, butadiene and styrene; and mixtures thereof. Preferred as alkylene carbonates are ethylene carbonate and propylene carbonate.

The alcohol used in the method for the catalytic conversion of dialkyl carbonate may be aromatic, such as phenol, or non-aromatic such as an $C_1$–$C_5$ alkyl alcohol, in particular methanol.

The lanthanum catalyst may be produced using any suitable method.

In a preferred embodiment the lanthanum catalyst is obtainable by the steps of:

i. loading (preferably by impregnation) the support with a lanthanum salt; and
ii. drying and calcining the impregnated support.

In this embodiment the support has a pre-shaped form. This form may be globular, circular cylinders and/or any desired or arbitrary moulded or extruded form, including monolythic form such as honeycomb or foam, or even a powder with a average particle size suitable for carrying out the reaction such as larger than about 100 $\mu$m. This support is impregnated via a gas phase and/or liquid phase with a lanthanum salt or lanthanum. After impregnation the impregnated support is if desired dried and subsequently calcined. Calcination is generally carried out at a calcination temperature between from about 120 to about 700° C. In view of the catalyst reactivity it is preferred to calcine at a calcination temperature in the range of from about 350 to about 600° C.

The lanthanum catalyst may also be obtained in a process in which the support itself is formed by precipitation. After precipitation formation of the support or concomitantly by coprecipitation a precipitate is formed comprising lanthanum salt in the required amount. After (co)precipitation of support and lanthanum salt the precipitate is calcined preferably under the above given calcination conditions. If required prior to calcination any solvent present may be removed by an intermediate drying step. Obviously, any prior art method for providing a lanthanum catalyst comprising a lanthanum compound supported on a support, may be used as long as it results in a catalyst which shows the catalytic conversion activity for use in the method according to the present invention.

As indicated above, the catalytic conversion may comprise hydrolysis, alcoholysis or the two catalytic conversion reactions concomitantly or consecutively. The hydrolysis is preferably carried out in a medium comprising water. The alcoholysis is preferably carried out in a reaction mixture comprising solely or to a high extent alcohol, in particular methanol.

In the alcoholysis any alkyl or aromatic alcohol may be used. The alkyl alcohol may be a primary, secondary and/or tertiary alcohol having preferably a $C_1$–$C_5$ alkyl group, more preferably a $C_1$–$C_3$ alkyl group. Most preferred is methanol. As an aromatic alcohol phenol may be used.

If the method according to the invention comprises a catalytic conversion by hydrolysis and alcoholysis then generally the molar ratio between water and alcohol lies between about 1:1 and about 1:100, preferably between about 1:5 and about 1:20.

Although the method for the catalytic conversion is suitable for any dialkyl carbonate conversion, it is preferred to use as a dialkyl carbonate an alkylene carbonate such as ethylene carbonate and propylene carbonate. Propylene carbonate is most preferred. In the alcoholysis the use of methanol is preferred. The combined hydrolysis and alcoholysis in the catalytic conversion according to the method of the invention results in a flexibility in the production of the corresponding diols and dialkyl carbonate together (alcoholysis) or to a production directed to the diol predominantly or solely with the simultaneous formation and release of carbon dioxide.

A further aspect of the invention relates to the use of the lanthanum catalyst for alcoholysis, hydrolysis or alcoholysis and hydrolysis of dialkyl carbonates, in particular of alkylene carbonates such as ethylene carbonate and propylene carbonate.

Hereafter mentioned and other aspects of the method and use according to the present invention and further advantages are illustrated by reference to examples. These examples are given for further illustration of the invention and are not considered as a limitation of the invention.

EXAMPLE 1

Catalyst Preparation

The catalysts were prepared by incipient wetness impregnation of 1.6 mm $SiO_2$ cylinders as support (pore volume of 1.04 ml/g, BET surface area of 56 $m^2$/g) with 1.37 mmol/g of support of various active elements, mostly as nitrate salt. The cylinders were then dried at 120° C., calcined for 2 hours at a temperature of 600° C. and crushed to a fraction of 30–80 mesh.

A very similar procedure was adopted for impregnating various supports with lanthanum nitrate. The lanthanum salt, the lanthanum loading and calcination temperature were varied.

EXAMPLE 2

Catalyst Testing—Metal Oxides

Catalytic testing is performed in a so-called 6 tubular nanoflow unit. This unit has 6 quartz reactors with an internal diameter of 3 mm. Each reactor was loaded with 0.15 gram of catalyst (0.2–0.6 mm diameter) that were diluted in 0.45 gram of SiC (0.05 mm diameter). 0.45 g of SiC were placed on top of this bed and used as feed pre-heater.

Once loaded, the catalysts were dried in situ under $N_2$-flow at 120° C. and atmospheric pressure for 1 hour. The reactors were then pressurized to 25 bar and a 4:1 molar mixture of methanol and propene carbonate was fed to the reactor at a flow rate of 5 gr/(gr cat*hr), together with an $N_2$ flow of 1.7 nL/(gr cat*hr). Occasionally, the feed consisted in a methanol:water:PC (propylene carbonate) mixture of 3.8:0.2:1 molar ratio or of a water:PC mixture of 1:3 molar ratio.

After an initial period of 20 hours at 120° C., the reactors were operated for 24 h, during which the liquid products were continuously condensed for off-line product analysis. The reactor temperature was then raised to 160° C. for 16 hours to simulate an enhanced deactivation and metal leaching.

In the following examples, the conversion of methanol and yield of dimethyl carbonate (DMC) are based on the molar amounts of these compounds divided by the molar amount of methanol supplied times 100%. The yield of PC to monopropyleneglycol(MPG) and/or methylpropanylcarbonate (MPC in mol %) is based on the molar amount of recovered PC divided by the molar amount of PC supplied in the feed times 100%.

TABLE 1

Performance of $La_2O_3$ supported on $SiO_2$, compared to other metal oxide supported on $SiO_2$ (metal loading of 1.37 mmole metal per g support)

| Catalyst Metal | Conv. MeOH [a] | PC [b] | Yield DMC [a] | MPG [b] | MPC [b] | DMC: MPG [c] | Leaching [d] |
|---|---|---|---|---|---|---|---|
| La Gr. III | 15.6 | 23.5 | 4.9 | 22.4 | 1.1 | 0.88 | 0.5 |
| Y | 11.9 | 11.1 | 4.0 | 11.1 | 0.0 | 1.44 | — |
| Ce Gr. II | 4.9 | 5.7 | 0.4 | 1.4 | 4.2 | 1.14 | — |
| Ca | 15.7 | 23.2 | 4.3 | 19.2 | 4.0 | 0.90 | 80 |
| Ba Gr. I | 12.9 | 19.5 | 3.5 | 15.8 | 3.7 | 0.89 | 63 |
| K | 8.6 | 11.4 | 1.6 | 5.8 | 5.6 | 1.10 | — |
| Cs | 8.5 | 11.1 | 1.6 | 6.0 | 5.0 | 1.07 | 68 |
| Nb | 4.4 | 5.8 | 0.5 | 1.2 | 4.4 | 1.67 | 0.32 |

[a] methanol and dimethylcarbonate (DMC) expressed in mole % based on methanol supplied in feed;
[b] propylene carbonate (PC) expressed in mole % based on propylene carbonate supplied in feed, monopropylene glycol (MPG) and methylpropanylcarbonate (MPC) expressed in mole % based on PC supplied in feed;
[c] expressed in mole:mole;
[d] mg of metal per kg of liquid product The examples reported in table 1 clearly show the exceptional performance of $La/SiO_2$ catalyst compared to $SiO_2$-supported catalysts based on metals that lie in the vicinity of La in the periodic table. In view of the heavy elements of group 1–5 of the periodic table La allows high MPG yield and a low metal leaching rate under the present enhanced leaching procedure.

Similar results have been obtained when using ethylene carbonate (EC) instead of propylene carbonate. Under the same operating conditions as applied for the examples of table 1, except for the ethylene carbonate which now substitutes the propylene carbonate in the feed, the $La/SiO_2$ catalyst converted EC to EG (ethylene glycol) with 38 mole % yield and a DMC/EG molar ratio of 0.91. By contrast the Y/SiO2 catalyst converted EC to EG with only 22 mole % yield and a DMC/EG molar ratio of 0.89.

EXAMPLE 3

Catalyst Testing—Lanthanum Loading and Lanthanum Salts

The performance of lanthanum catalysts on various mineral supports and lanthanum catalysts obtained after impregnation of the $Al_2O_3$ support with various lanthanum salts have been tested.

TABLE 2

Performance of $La_2O_3$ supported on various mineral support (lanthanum loading of 15.5 wt. %, from $La(NO_3)_3$), and of $La/Al_2O_3$ catalysts based on various lanthanum salts (lanthanum loading of 15.5 wt. %)

| support or La-salt | Conv. MeOH [a] | PC [b] | Yield DMC [a] | MPG [b] | MPC [b] | DMC: MPG [c] | BET [d] |
|---|---|---|---|---|---|---|---|
| Al2O3 | 18.5 | 28.3 | 6.0 | 27.6 | 0.7 | 0.87 | 280 |
| SiO2 | 15.6 | 23.5 | 5.0 | 22.4 | 1.1 | 0.89 | 56 |
| MgO [e] | 14.0 | 21.0 | 4.4 | 19.8 | 1.2 | 0.89 | 53 |
| TiO2 | 8.9 | 12.0 | 2.7 | 10.8 | 1.2 | 1.00 | 70 |
| Effect of salt | | | | | | | |
| Nitrate | 14.4 | 21.9 | 4.0 | 18.7 | 3.2 | 0.86 | 280 |
| Chloride | 17.5 | 26.4 | 5.0 | 23.0 | 3.4 | 0.87 | 280 |
| Acetate | 18.1 | 27.5 | 5.3 | 24.1 | 3.4 | 0.87 | 280 |

[a] expressed in mole % based on methanol supplied in feed;
[b] expressed in mole % based on PC supplied in feed;
[c] expressed in mole:mole;
[d] BET surface area of the support in $m^2/g$;
[e] MgO is stabilized by $Al_2O_3$ in a Mg:Al molar ratio of 5:1

Table 2 shows that various supports are suitable, though supports with the highest surface area are most preferable. Similarly, various lanthanum salts can be used for preparing efficient supported lanthanum catalysts.

EXAMPLE 4

Catalyst Testing—Alcoholysis/Hydrolysis

The lanthanum catalyst according to the invention has been used in the catalytic conversion of dialkyl carbonate by methanolysis and hydrolysis. The lanthanum catalyst was supported on $Al_2O_3$ and $SiO_2$.

TABLE 3 performance of $Al_2O_3$- and $SiO_2$-supported lanthanum catalysts under MeOH:$H_2$O:PC feed (molar ratio of 3.8:0.2:1.0)

| Catalyst (loading wt. %) | Conv. MeOH [a] | PC [b] | Yield DMC [a] | MPG [b] | MPC [b] | DMC: MPG [c] |
|---|---|---|---|---|---|---|
| La/Al2O3 (8.6%) | 20.7 | 28.0 | 1.1 | 27.0 | 2.7 | 0.12 |
| La/Al2O3 (15.5%) | 32.3 | 32.2 | 1.5 | 27.8 | 3.2 | 0.16 |
| La/Al2O3 (26.3%) | 25.3 | 32.9 | 0.9 | 24.6 | 2.9 | 0.12 |
| La/SiO2 (8.6%) | 20.9 | 18.9 | 0.1 | 9.8 | 3.3 | 0.02 |
| La/SiO2 (15.5%) | 21.4 | 15.9 | 0.1 | 14.2 | 3.3 | 0.02 |
| La/SiO2 (26.3%) | 26.4 | 21.0 | 0.1 | 12.8 | 3.3 | 0.02 |

[a] expressed in mole % based on methanol supplied in feed;

TABLE 3-continued performance of $Al_2O_3$- and $SiO_2$-supported
lanthanum catalysts under $MeOH:H_2O:PC$ feed (molar ratio
of 3.8:0.2:1.0)

| Catalyst (loading wt. %) | Conv. MeOH [a] | PC [b] | Yield DMC [a] | MPG [b] | MPC [b] | DMC: MPG [c] |
|---|---|---|---|---|---|---|

[b] expressed in mole % based on PC supplied in feed;
[c] expressed in mole:mole Table 3 shows that lanthanum based catalyst can combine the methanolysis and hydrolysis of PC and, thereby, produce DMC/MPG in varying ratio, significantly below the 1:1 ratio reported above. Clearly, a small amount of water suffices to produce MPG in excess of DMC, particularly at lower conversion level, as is the case for the less active $SiO_2$-supported catalysts.

Lanthanum based catalysts are even suitable for hydrolyzing PC with water in absence of methanol. When operating with a feed of $PC:H_2O$ of 3:1 molar ratio at 100° C. and a WHSV of 5 g/g/h and an N2 flow of 2.1 g/g/h, a 15.5 w % $La/Al_2O_3$ converted PC to MPG at 24.9 mole % yield. No DMC was formed under these circumstances.

A similar hydrolysis experiments has also been carried out with the same lanthanum/alumina catalyst in the form of 1.3 mm trilobes. The operation conditions were 100° C. and a feed consisting of a PC:water mixture of 3:1 molar ratio introduced at the higher space velocity of WHSV=15 g/g/h and an N2 flow of 2.1 g/g/h. Under these conditions, the 1.3 mm trilobes allowed a MPG yield of 3.6 mole %. For comparison, the same catalyst reached an MPG yield of 5.2 mole % when employed as crushed powder of 0.2–0.6 mm.

EXAMPLE 5

Catalyst Testing—Alcoholysis with Phenol

In this example was carried out the alcoholysis of dimethyl carbonate (DMC) with phenol to produce methylphenyl-carbonate (MPC), a necessary intermediate in the production of diphenyl-carbonate. For this purpose a mixture of DMC and phenol with a molar ratio of 5:1 was passed onto a catalyst bed of 0.5 g of 15.5% $La/SiO_2$ at a weight hourly space velocity of 2 g/g cat/h, at atmospheric pressure and 400° C., together with an N2 flow of 2600 Nl/l cat./h. Consequently, MPC was produced with 32% yield and 90% selectivity, based on phenol.

What is claimed is:

1. A method for the catalytic conversion of an alkylene carbonate to its corresponding diols and a dialkyl carbonate comprising contacting the alkylene carbonate with an alcohol in the presence of a catalyst comprising at least about 7 wt. % of lanthanum supported on a support.

2. The method as claimed in claim 1, wherein the lanthanum catalyst comprises from about 7 wt. % to about 40 wt. % lanthanum per gram support.

3. The method as claimed in claim 1, wherein the support is selected from the group consisting of $Al_2O_3$, $SiO_2$, MgO, $TiO_2$, $ZrO_2$, ZnO and mixtures thereof.

4. The method as claimed in claim 1, wherein the lanthanum catalyst is obtainable by the steps of:
  i. loading the support with a lanthanum salt; and
  ii. drying and calcining the impregnated support.

5. The method as claimed in claim 4, wherein the lanthanum salt is selected from the group consisting of lanthanum chloride, lanthanum acetate and lanthanum nitrate.

6. The method as claimed in claim 1, wherein the alkylene carbonate is propylene carbonate and the alcohol is methanol.

7. The method as claimed in claim 1, wherein the lanthanum catalyst comprises from about 8 wt % to about 30 wt % of lanthanum per gram of support.

8. The method of claim 1 comprising contacting the alkylene carbonate with water in addition to an alcohol.

9. A method for the catalytic conversion of an alkylene carbonate to predominately its corresponding diols comprising contacting the alkylene carbonate with water in the presence of a catalyst comprising at least about 7 wt. % of lanthanum supported on a support.

10. The method as claimed in claim 9, wherein the lanthanum catalyst comprises from about 7 wt. % to about 40 wt. % lanthanum per gram support.

11. The method as claimed in claim 9, wherein the support is selected from the group consisting of $Al_2O_3$, $SiO_2$, MgO, $TiO_2$, $ZrO_2$, ZnO and mixtures thereof.

12. The method as claimed in claim 9, wherein the lanthanum catalyst is obtainable by the steps of:
  i. loading the support with a lanthanum salt; and
  ii. drying and calcining the impregnated support.

13. The method as claimed in claim 12, wherein the lanthanum salt is selected from the group consisting of lanthanum chloride, lanthanum acetate and lanthanum nitrate.

14. The method as claimed in claim 9, wherein the lanthanum catalyst comprises from about 8 wt. % to about 30 wt % of lanthanum per gram of support.

* * * * *